United States Patent [19]

Grey

[11] Patent Number: 5,892,066

[45] Date of Patent: Apr. 6, 1999

[54] PROPYLENE OXIDE AND DERIVATIVES PROCESS

[75] Inventor: Roger A. Grey, West Chester, Pa.

[73] Assignee: ARCO Chemical Technology, L.P., Greenville, Del.

[21] Appl. No.: 989,788

[22] Filed: Dec. 12, 1997

[51] Int. Cl.$^6$ .......................... C07D 301/06; C07C 31/18
[52] U.S. Cl. .......................... 549/532; 568/852; 568/860; 568/895
[58] Field of Search .......................... 549/532; 568/852, 568/860, 895

[56] References Cited

U.S. PATENT DOCUMENTS

| | | | |
|---|---|---|---|
| 2,767,221 | 10/1956 | Ballard et al. | 260/638 |
| 3,071,601 | 1/1963 | Aries | 260/348.5 |
| 3,338,800 | 8/1967 | Binning et al. | 203/52 |
| 3,350,421 | 10/1967 | Binning et al. | 260/348.5 |
| 3,428,658 | 2/1969 | Kassal et al. | 260/348.5 |
| 3,957,690 | 5/1976 | Bobolev et al. | 252/462 |
| 4,012,424 | 3/1977 | Sherwin et al. | 260/348 R |
| 4,226,780 | 10/1980 | Fouquet et al. | 260/348.16 |

FOREIGN PATENT DOCUMENTS 215084  10/1984  Germany .

OTHER PUBLICATIONS

Chem Abstracts, vol. 33, p. 1674 (1939).

*Primary Examiner*—Alan L. Rotman
*Assistant Examiner*—Charanjit S. Aulakh
*Attorney, Agent, or Firm*—William C. Long

[57] ABSTRACT

Propylene is oxidized with molecular oxygen in the liquid phase to form products including propylene oxide, propylene glycol, propylene glycol esters, allyl alcohol, acrolein and acetal, the acrolein is hydrogenated to allyl alcohol, the acetol is hydrogenated to propylene glycol, the propylene glycol esters are hydrolyzed to propylene glycol, and propylene oxide, propylene glycol and allyl alcohol are recovered as products.

7 Claims, 1 Drawing Sheet

PROPYLENE OXIDE AND DERIVATIVES PROCESS

BACKGROUND OF THE INVENTION

The present invention relates to a process for the production of propylene oxide by direct molecular oxygen oxidation of propylene and to the formation and recovery of various propylene oxide derivatives and coproducts.

FIELD OF THE INVENTION

The molecular oxygen oxidation of propylene to form propylene oxide together with various other oxidation products is a known reaction. Various patents describing this reaction and separation procedures for recovering oxidation products include U.S. Pat. Nos. 3,071,601, 3,338,800, 3,350,421, 3,428,658, 3,957,690, and the like, as well as East German 215,084 and the like.

SUMMARY OF THE INVENTION

In accordance with the invention, propylene is oxidized in the liquid phase with molecular oxygen to form propylene oxide together with other products including propylene glycol and propylene glycol precursors, acrolein and allyl alcohol and various other products. The propylene glycol precursors are converted to propylene glycol by hydrolysis and hydrogenation procedures and this propylene glycol can be combined with propylene glycol produced directly during the oxidation. Acrolein is hydrogenated to allyl alcohol and this product can be combined with the allyl alcohol produced directly during the oxidation. Various other products may be recovered or may be recycled to the oxidation to enhance yields of products such as propylene oxide.

BRIEF DESCRIPTION OF THE DRAWING

The attached drawing illustrates schematically practice of the invention.

DETAILED DESCRIPTION

Figure 1:
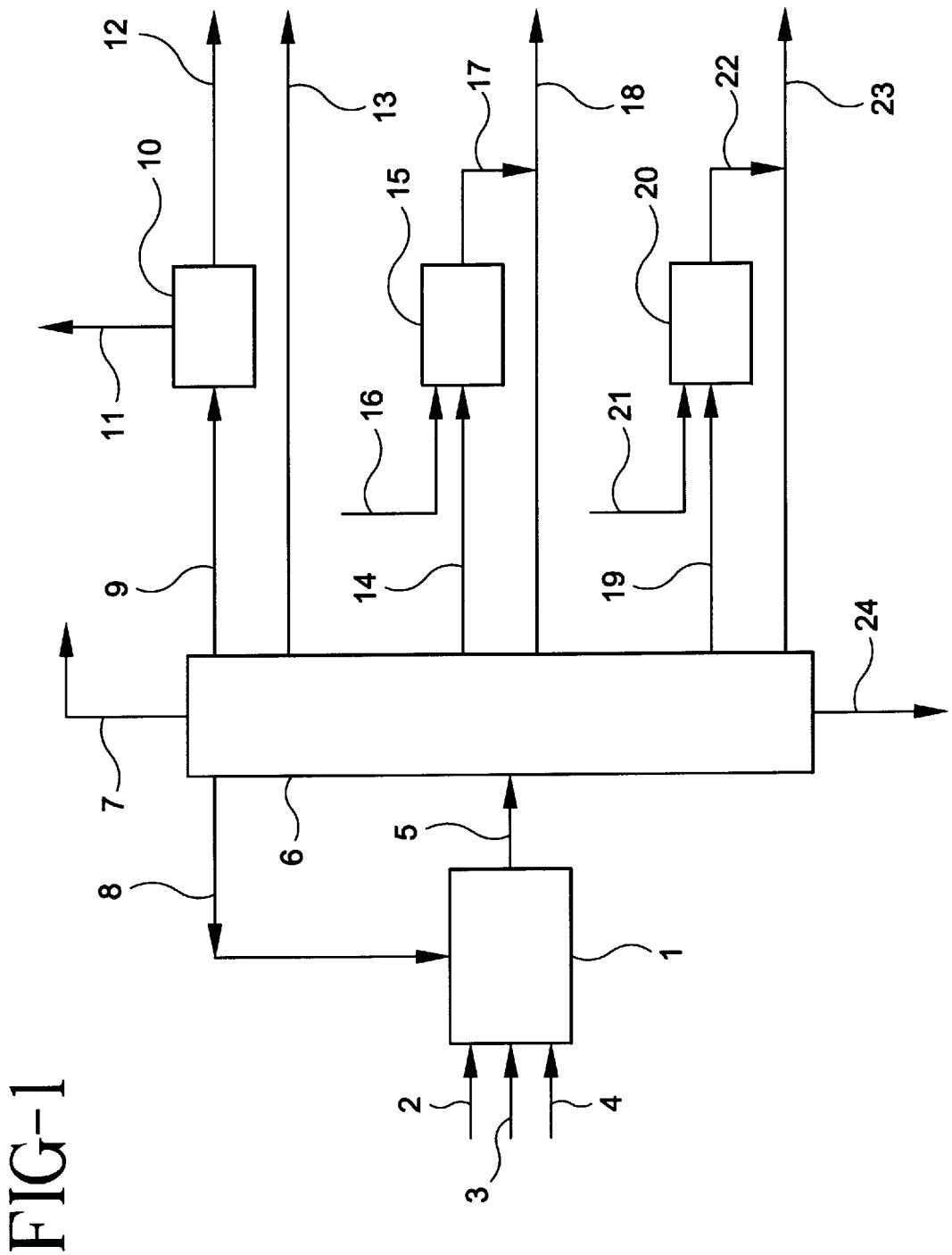

According to the invention, propylene is oxidized in the liquid phase in accordance with known procedures to form a mixture of reaction products including propylene oxide, propylene glycol and precursors of propylene oxide and/or propylene glycol such as acetol, propylene glycol mono-acetates and di-acetate, propylene glycol, mono-formates and di-formate, allyl alcohol and its precursor acrolein, acetic and formic acids, acetaldehyde, and various other products.

In the process of the invention, the overall production of the highly valuable propylene oxide, propylene glycol, and allyl alcohol is maximized so as to provide a process having highly favorable economics.

Referring to the accompanying drawing, propylene and molecular oxygen are reacted in reaction zone 1 in accordance with known conditions to form propylene oxide. The reaction is carried out in the liquid phase and a solvent is suitably employed. Propylene is introduced via line 2, oxygen via line 3 and solvent via line 4.

The reaction mixture passes via line 5 to distillation zone 6 wherein it is resolved into various components. Zone 6 is depicted schematically as a single zone whereas generally it is a plurality of fractional distillation zones. The product lines from zone 6 do not necessarily reflect the relative boiling points of the various components.

Carbon monoxide and carbon dioxide formed during the oxidation are separated via line 7. Acetaldehyde and unreacted propylene are separated via line 8 and are suitably recycled to reaction zone 1, the acetaldehyde acting therein to promote the formation of propylene oxide.

Propylene glycol mono-and di-formate and acetate esters pass via line 9 to hydrolysis zone 10 wherein they are hydrolyzed to propylene glycol by known procedures. Acetic and formic acid are depicted as being recovered via line 11 and propylene glycol via line 12.

In a less preferred practice, propylene glycol formate and acetate can be cracked to propylene oxide and acetic formic acid in accordance with known procedures. See U.S. Pat. No. 4,012,424 to Chem Systems.

Propylene oxide formed by molecular oxygen oxidation in zone 1 is separated from distillation zone 6 via line 13 and is recovered as an essential product of the process.

Acrolein formed in zone 1 is separated from distillation zone 6 via line 14 and passes to hydrogenation zone 15 wherein it is converted to allyl alcohol in accordance with known procedures; see PEP Report 58. Hydrogen gas or isopropanol as a hydrogen source is introduced via line 16. Product allyl alcohol from zone 15 passes via line 17 and is suitably combined with allyl alcohol produced in reaction zone 1 which is separated from distillation zone 6 via line 18.

Acetol formed in zone 1 is separated from distillation zone 6 via line 19 and passes to hydrogenation zone 20 wherein it is converted to propylene glycol in accordance with known procedures, hydrogen being introduced via line 21. See, for example, Ber. 71B, 2712–16, (1938). Product propylene glycol from zone 20 passes via line 22 and is suitably combined with propylene glycol produced in reaction zone 1 which is separated from distillation zone 6 via line 23.

Various other products of the oxidation in zone 1 including methane, methanol methyl formate, ethanol, propanol, isopropanol, acetone, acetic and formic acids, acrylic acid and formaldehyde are separated via line 24 from zone 6. These products can be used as fuel or alternatively depending upon the current economics can be individually recovered.

In accordance with the invention, propylene and oxygen are reacted to form propylene oxide and a number of other oxidation products. The reaction is carried out in the liquid phase at temperatures illustratively in the range 80° to 220° C., preferably 130° to 170° C., most preferably 145° to 155° C., and at pressures ranging from 400 to 1800 psig, preferably 600 to 1100 psig. It is preferred to use a solvent during the reaction, illustrative solvents being acetone, acetonitrile, benzonitrile, acetophenone, propylene carbonate, tertiary butyl benzene, and the like. Preferable the solvent comprises 20–60 wt % of the solvent plus propylene.

The reaction is conducted so as to provide a propylene conversion of about 1 to 30%, preferably 3 to 10%.

Both continuous and batch oxidation procedures can be used, continuous procedures being preferred. An illustrative range of oxidation products resulting from this oxidation is shown in the following table. Oxidizing feed gas comprised by volume of 5 to 100% oxygen with the remainder an inert such as nitrogen is used. In accordance with known procedures, the reaction can be carried out in the presence or absence of catalysts or radical initiators.

TABLE 1

| COMPOUND | SELECTIVITY[1] RANGE |
| --- | --- |
| Acetaldehyde | 1 to 20 |
| Methyl Formate | 0.1 to 2 |
| Methanol | 0.1 to 5 |
| Propylene Oxide | 25 to 65 |
| Ethanol | 0.1 to 5 |
| Acrolein | 0 to 15 |

TABLE 1-continued

| COMPOUND | SELECTIVITY[1] RANGE |
|---|---|
| Acetone | 0.1 to 10 |
| Isopropanol | 0.1 to 10 |
| N-Propanol | 0 to 5 |
| Allyl Alcohol | 0.1 to 20 |
| Trimethyl Dioxolane | 0 to 5 |
| Acetol | 0 to 20 |
| Propylene Glycol | 0 to 20 |
| PG Formate Ester | 0 to 10 |
| 4-Hydroxybutanone | 0 to 5 |
| PG Acetate Ester | 0 to 10 |
| Carbon Dioxide | 5 to 40 |
| Carbon Monoxide | 0 to 35 |
| Methane | 0 to 10 |
| Acetic Acid | 0 to 25 |
| Formic Acid | 0 to 25 |
| Acrylic Acid | 0 to 15 |
| Formaldehyde | 0 to 5 |

[1]Selectivity = Millimoles of named product on a propylene basis/sum of all observed organic products on a propylene basis.

Products of the oxidation are appropriately resolved by distillation in one but preferably a plurality of fractionation zones. Solvent and unreacted propylene are recycled to the oxidation zone together with acetaldehyde which is an oxidation product and which promotes the oxidation when recycled to the oxidation zone.

Propylene oxide is, of course, the main product of the oxidation and is recovered as such by distillation.

Propylene glycol monoacetate and monoformate as well as diacetate and diformate are recovered by distillation and hydrolyzed to the glycol. Alternatively, the monoacetate and monoformate can be converted in accordance with known procedures to propylene oxide and acetic and/or formic acid by pyrolysis. A description of appropriate conditions for this pyrolysis can be found, for example, in PEP Report No. 70A and illustratively involve cracking temperatures of 385° C., the use of xylene solvent (1:1 by weight xylene to monocetate sodium borate catalyst) and achieve selectivities in excess of 70% to propylene oxide. See also U.S. Pat. No. 4,012,424. Other pyrolysis products such as acetone, acetic acid and formic acid are recovered as by distillation and represent valuable coproducts.

Acrolein is recovered from the oxidation product mixture by distillation and hydrogenated to allyl alcohol. Both liquid and vapor phase processes have been developed, the vapor phase procedures conveniently use a large excess of hydrogen at 200°–300° C. at high pressures with a mixed copper cadmium catalyst; yields of 50–70% have been achieved. In a liquid phase process using a catalyst containing organic acid salts of copper and cadmium, selectivity to allyl alcohol has been 70–74%. Product allyl alcohol is recovered from the hydrogenation mixture as by distillation as are other products such as propionaldehyde. Isopropanol which is formed during the oxidation can be used as a hydrogen source.

Acetol is recovered from the oxidation reaction mixture and hydrogenated in the presence of a base such as calcium hydroxide and a nickel/chromium catalyst, for example, at 50 atmospheres hydrogen pressure at 80° C. to form propylene glycol product.

EXAMPLES

The liquid phase oxidation of propylene is illustrated by the following examples:

Example 1

This reaction is conducted in a one liter autoclave equipped with a condenser and back pressure regulator so that the propylene, liquid products and solvent are returned to the reactor and the noncondensable gases are continuously purged from the reactor. The reactor is initially charged with 220 grams of acetone, 130 grams of propylene and 800 psig of 10% $O_2/N_2$. The back pressure regulator is set at 1100 psig. The reaction is heated to 150° C. and then additional propylene is fed to the reactor at 10 grams/hr and 10% $O_2/N_2$ is fed to the reactor at 800 cc/min. After 75 minutes at these conditions the reaction is cooled to 23° C. Liquid and overhead gas GC samples were taken at 15 and 75 minutes. The gases from the bulk reaction mixture were vented into gas bags and the contents analyzed by GC. The bulk liquid was removed from the reactor and analyzed by GC, LC and chemical analyses for organic products and water. The attached table lists the products found and the selectivities.

Example 2

This reaction is conducted in a one liter autoclave equipped with a condenser and back pressure regulator so that the propylene, liquid products and solvent are returned to the reactor and the noncondensable gases are continuously purged from the reactor. The reactor is initially charged with 230 grams of acetonitrile, 136 grams of propylene and 800 psig of 10% $O_2/N_2$. The back pressure regulator is set at 1100 psig. The reaction is heated to 150° C. and then additional propylene is fed to the reactor at 40 grams/hr and 10% $O_2/N_2$ is fed to the reactor at 800 cc/min. After 60 minutes at these conditions the reaction is cooled to 23° C. Liquid and overhead gas GC samples were taken at 15 and 60 minutes. The gases from the bulk reaction mixture were vented into gas bags and the contents analyzed by GC. The bulk liquid was removed from the reactor and analyzed by GC, LC and chemical analyses for organic products and water. The attached table lists the products found and the selectivities.

TABLE II

| COMPOUND | EXAMPLE 1 SELECTIVITY[1] IN ACETONE | EXAMPLE 2 SELECTIVITY[1] IN ACETONITRILE |
|---|---|---|
| ACETALDEHYDE | 5 | 6.8 |
| METHYL FORMATE | 0.8 | 1.1 |
| METHANOL | 2.2 | 2.0 |
| PROPYLENE OXIDE | 43.7 | 47 |
| ETHANOL | 0.6 | 0.4 |
| ACROLEIN | 2.5 | 1.3 |
| ACETONE | — | 7.1 |
| ISOPROPANOL | 2.7 | 3.1 |
| N-PROPANOL | 0.3 | 0.1 |
| ALLYL ALCOHOL | 4.2 | 4.6 |
| TRIMETHYL DIOXOLANE | 0.3 | 0 |
| ACETOL | 4.6 | 5.2 |
| PROPYLENE GLYCOL | 0.3 | 2.2 |
| PG FORMATE ESTER | 0.6 | 0.5 |
| 4-HYDROXYBUTANONE | 0.2 | 0 |
| PG ACETATE ESTER | 0.4 | 0.1 |
| CARBON DIOXIDE | 8.7 | 9.3 |
| CARBON MONOXIDE | 3.9 | 2.8 |
| METHANE | 0.3 | 0.3 |
| ACETIC ACID | 5.7 | 3.2 |
| FORMIC ACID | 8.6 | 6.1 |
| ACRYLIC ACID | 0.5 | 0.2 |
| FORMALDEHYDE | 0.6 | 0.3 |

[1]SELECTIVITY = MILLIMOLES OF NAMED PRODUCT ON A PROPYLENE BASIS/SUM OF ALL OBSERVED ORGANIC PRODUCTS ON A PROPYLENE BASIS

Example 3

The liquid reaction mixture from a number of repetitions of Example 1 is distilled in accordance with known procedures to separate the various components in a series of separate distillation zones as described in German Patent 215,084, the disclosure of which is herein incorporated by reference.

Following the distillation procedure of Ger 215,084, about 120 g of propylene are separated overhead from column 1; the propylene can be used in subsequent oxidations.

Acetaldehyde is recovered in amount of 0.7 g as overhead from column 4 and also can be used in subsequent oxidations to enhance propylene oxide production.

The propylene oxide product of the oxidation is recovered in amount of 5.6 g as overhead from column 8 and comprises a valuable product of the process.

Acrolein formed during the oxidation is contained in the overhead product from column 9 along with methyl acetate, methanol, isopropanol and allyl alcohol. This mixture is hydrogenated in the vapor phase over a copper/cadmium catalyst at 300° C. whereby the acrolein is converted to allyl alcohol. The hydrogenation product is combined with the bottoms from column 9 and passed to column 10 wherein product allyl alcohol formed both in the oxidation reactor and in the above hydrogenation is separated in amount of 0.755 g as a product of the process. The remaining components may be separately recovered or may be used for fuel values.

The bottoms stream from column 1 passes to column 3 as described in the German patent and the bottoms stream from column 3 comprises propylene glycol and esters there of as well as acetol. It is possible in accordance with the invention to crack the esters to propylene oxide in accordance with the procedures of U.S. Pat. No. 4,012,424 after first recovering acetol, but in preferred practice, the bottoms from column 3 is hydrogenated in the presence of calcium hydroxide and a Ni/Cr catalyst in accordance with known procedures to convert the acetol to propylene glycol.

After hydrogenation, the resulting stream is passed a hydrolysis zone (not shown) wherein propylene glycol esters are converted to propylene glycol and thence to column 15 as described in German 215,084 and distilled as described thereon. Product propylene glycol is recovered as bottoms from column 17 in amount of 0.94 g.

As a result of practice of the invention, the yield of allyl alcohol is increased by a factor of 1.385 while the yield of propylene glycol is increased by a factor of 20.5 and accordingly the overall process economics are substantially improved.

I claim:

1. The process which comprises:

a) oxidizing propylene in the liquid phase with molecular oxygen to form a product mixture comprised of propylene oxide, propylene glycol, propylene glycol formate and acetate, allyl alcohol, acrolein and acetol, b) separating propylene oxide from the oxidation reaction mixture, c) separating propylene glycol from the oxidation reaction mixture, d) separating allyl alcohol from the oxidation reaction mixture, e) separating mono- and di-propylene glycol acetates and formates from the oxidation reaction mixture and hydrolyzing the separated propylene glycol acetates and formates to form product propylene glycol and recovering the thusly formed propylene glycol, f) separating acrolein from the oxidation reaction mixture, hydrogenating the separated acrolein to form product allyl alcohol and recovering the thusly formed allyl alcohol, g) separating acetol from the oxidation reaction mixture, hydrogenating the separated acetol to form product propylene glycol and recovering the thusly formed propylene glycol.

2. The process of claim 1 wherein a mixture of molecular oxygen and inert gas is used in step a).

3. The process of claim 1 carried out in a continuous manner.

4. The process of claim 1 wherein acetaldehyde is also formed in step a) and is separated from the product mixture and recycled to step a).

5. The process of claim 1 wherein a solvent is used in step a) in amount of 20 to 60% by weight of solvent plus propylene.

6. The process of claim 1 wherein at least a portion of the mono-propylene glycol acetate and/or the mono-propylene glycol formate is cracked to form propylene oxide.

7. The process of claim 1 wherein additional products of the oxidation of step a) including isopropyl alcohol, acetone, methyl formate, formic acid, acetic acid, and the like are separately recovered.

* * * * *